US010675292B2

(12) United States Patent
Van Wijk et al.

(10) Patent No.: US 10,675,292 B2
(45) Date of Patent: Jun. 9, 2020

(54) METHOD FOR REDUCING WHITE MATTER LESIONS, WHITE MATTER HYPERINTENSITIES (WMH), LEUKOARAIOSIS OR PERIVENTRICULAR WHITE MATTER DISEASE IN ELDERLY

(71) Applicant: N.V. Nutricia, Zoetermeer (NL)

(72) Inventors: Nick Van Wijk, Utrecht (NL); Robert Johan Joseph Hageman, Utrecht (NL); Mehmet Cansev, Bursa (TR)

(73) Assignee: N.V. NUTRICIA, Zoetermeer (NL)

( * ) Notice: Subject to any disclaimer, the term of this patent is extended or adjusted under 35 U.S.C. 154(b) by 10 days.

(21) Appl. No.: 15/115,487

(22) PCT Filed: Feb. 2, 2015

(86) PCT No.: PCT/NL2015/050065
§ 371 (c)(1),
(2) Date: Jul. 29, 2016

(87) PCT Pub. No.: WO2015/115899
PCT Pub. Date: Aug. 6, 2015

(65) Prior Publication Data
US 2017/0157164 A1    Jun. 8, 2017

(30) Foreign Application Priority Data

Jan. 31, 2014  (WO) ............... PCT/NL2014/050058

(51) Int. Cl.
| | |
|---|---|
| *A61K 31/7068* | (2006.01) |
| *A61K 31/7072* | (2006.01) |
| *A61K 31/14* | (2006.01) |
| *A61K 31/202* | (2006.01) |
| *A61K 31/355* | (2006.01) |
| *A61K 31/375* | (2006.01) |
| *A61K 31/4415* | (2006.01) |
| *A61K 31/519* | (2006.01) |
| *A61K 31/683* | (2006.01) |
| *A61K 31/714* | (2006.01) |
| *A61K 33/04* | (2006.01) |
| *A61K 45/06* | (2006.01) |
| *A61K 31/685* | (2006.01) |

(52) U.S. Cl.
CPC .......... *A61K 31/7068* (2013.01); *A61K 31/14* (2013.01); *A61K 31/202* (2013.01); *A61K 31/355* (2013.01); *A61K 31/375* (2013.01); *A61K 31/4415* (2013.01); *A61K 31/519* (2013.01); *A61K 31/683* (2013.01); *A61K 31/685* (2013.01); *A61K 31/7072* (2013.01); *A61K 31/714* (2013.01); *A61K 33/04* (2013.01); *A61K 45/06* (2013.01)

(58) Field of Classification Search
CPC .... A61K 31/14; A61K 31/202; A61K 31/355; A61K 31/375; A61K 31/4415; A61K 31/519; A61K 31/683; A61K 31/7068; A61K 31/7072; A61K 31/714; A61K 33/04
USPC ....................................................... 424/702
See application file for complete search history.

(56) References Cited

U.S. PATENT DOCUMENTS

| | | | |
|---|---|---|---|
| 7,384,981 B2 * | 6/2008 | Kiliaan ................. | A61K 31/14 424/617 |
| 2005/0203053 A1 | 9/2005 | Wurtman et al. | |
| 2011/0105594 A1 * | 5/2011 | De Kort ............ | A61K 31/7052 514/44 R |
| 2013/0136800 A1 * | 5/2013 | Gil Hernandez .... | A61K 31/221 424/602 |

FOREIGN PATENT DOCUMENTS

| | | | |
|---|---|---|---|
| EP | 1 800 675 A1 | 6/2007 | |
| WO | WO-00/06174 A1 | 2/2000 | |
| WO | WO-2007/089703 A2 | 8/2007 | |
| WO | WO-2009/002148 A1 | 12/2008 | |
| WO | WO-2009/002165 A1 | 12/2008 | |
| WO | WO-2009/002166 A1 | 12/2008 | |
| WO | WO-2009/059306 A1 | 5/2009 | |
| WO | WO 2009059306 A1 * | 5/2009 | ............. A61K 49/10 |
| WO | WO-2012/125020 A1 | 9/2012 | |
| WO | WO 2012125020 A1 * | 9/2012 | ........... A61K 9/0095 |
| WO | WO-2013/066151 A1 | 5/2013 | |
| WO | WO-2013/066152 A1 | 5/2013 | |
| WO | WO-2013/066165 | 5/2013 | |

(Continued)

OTHER PUBLICATIONS

Xiong et al. (J Aging Res. 2011, Published online Aug. 23, 2011).*

(Continued)

*Primary Examiner* — Ali Soroush
*Assistant Examiner* — Courtney A Brown
(74) *Attorney, Agent, or Firm* — Foley & Lardner LLP

(57) ABSTRACT

The invention pertains to the use of one or more of uridine and cytidine, or salts, phosphates, acyl derivatives or esters thereof in the manufacture of a composition for treating, preventing or reducing the risk of occurrence of white matter lesions, white matter hyperintensities (WMH), Leukoaraiosis or periventricular white matter disease in elderly not suffering from a neurodegenerative disorder, preferably non-demented elderly and elderly not suffering from Alzheimer's Disease. It was found that with the compositions according to the invention Nogo-A protein levels could be controlled, particularly suppressed or reduced.

14 Claims, 2 Drawing Sheets

(56) References Cited

FOREIGN PATENT DOCUMENTS

| WO | WO-2013/066167 | 5/2013 | |
| WO | WO 2013066152 A1 * | 5/2013 | ............. A61K 45/06 |

OTHER PUBLICATIONS

Castaño et al., Neurochemistry International, 62(2013), 145-156.*
Berlow et al., International Journal of Geriatric Psychiatry, Jul. 2010, vol. 25, Issue 8, abstract.*
De Waal et al., "The effect of souvenaid on functional brain network organization in patients with mild Alzheimer's Disease: a randomized controlled study", PLOS ONE, Jan. 2014, vol. 9, Issue 1, pp. 2-11.
Schef et al., "Glucose metabolism, gray matter structure, and memory decline in subjective memory impairment", Neurology, Sep. 25, 2012, vol. 79, pp. 1332-1339.
Schwab et al., "Functions of Nogo proteins and their receptors in the nervous system", Nature Reviews Neuroscience, Dec. 2010, vol. 11, pp. 799-811.
Wang et al., "Nogo-A is associated with secondary degeneration of substantia nigra in hypertensive rats with focal cortical infarction", Brain Research, 2012, vol. 1469, pp. 153-163.
Ward et al., "Docosahexaenoic acid prevents white matter damage after spinal cord injury", Journal of Neurotrauma, Oct. 2010, vol. 27, pp. 1769-1780.
International Search Report issued in International Patent Application No. PCT/NL2015/050064, dated Jul. 1, 2015.
International Search Report issued in International Patent Application No. PCT/NL2015/050065, dated Jun. 25, 2016.
Anonymous, Compound 'cocktail' improves brain function in rodents, Treatment is undergoing a clinical study in Alzheimer's patients, MIT, vol. 52, No. 10 Wednesday, Nov. 28, 2007.
Hampel et al., Total and Phosphorylated Tau Protein as Biological Markers of Alzheimer's Disease, Exp Gerontol. Jan. 2010; 45(1): 30.
Silverman et al., Positron Emission Tomography in Evaluation of Dementia Regional Brain Metabolism and Long-term Outcome, JAMA, Nov. 7, 2001—vol. 286, No. 17.

* cited by examiner

METHOD FOR REDUCING WHITE MATTER LESIONS, WHITE MATTER HYPERINTENSITIES (WMH), LEUKOARAIOSIS OR PERIVENTRICULAR WHITE MATTER DISEASE IN ELDERLY

CROSS-REFERENCE TO RELATED APPLICATIONS

This application is the National Phase of International Patent Application No. PCT/NL2015/050065, filed Feb. 2, 2015, published on Aug. 6, 2015 as WO 2015/115899 A1, which claims priority to International Patent Application No. PCT/NL2014/050058, filed Jan. 31, 2014. The contents of these applications are herein incorporated by reference in their entirety.

The invention is in the field of medical nutrition and more particularly relates to a composition for treating, preventing or reducing the risk of occurrence of white matter lesions, white matter hyperintensities (WMH), Leukoaraiosis or periventricular white matter disease and treating/preventing/reducing the risk of hippocampus dysfunction in elderly not suffering from a neurodegenerative disorder, preferably non-demented elderly and elderly not suffering from Alzheimer's Disease. In one aspect, the invention pertains to controlling, preferably reducing or suppressing Nogo-A protein levels in elderly not suffering from a neurodegenerative disorder, preferably non-demented elderly and elderly not suffering from Alzheimer's Disease.

BACKGROUND OF THE INVENTION

During the last decennium, uridine, choline and omega-3 fatty acids such as DHA have attracted attention as active components in treating cognitive dysfunction and age-associated memory impairment (AAMI), see e.g. WO2007/089703 (Massachusetts Institute of Technology) and WO 2009/002165 (N.V. Nutricia). These compounds are rate-limiting precursors for membrane phosphatide synthesis. According to the above applications, by improving the membrane phosphatide synthesis, it is believed to improve cognitive or memory function. The effects on membrane phospholipids have been associated with enhancement in specific pre- and post-synaptic proteins.

WO 2013/066165 and WO 2013/066167 (N.V. Nutricia) disclose a product comprising (i) one or more of uridine and cytidine, or salts, phosphates, acyl derivatives or esters thereof, and (ii) a lipid fraction comprising at least one of docosahexaenoic acid 5 (22:6; DHA), eicosapentaenoic acid (20:5; EPA) and docosapentaenoic acid (22:5; DPA), or esters thereof, recognition and executive functions like speed of information processing, cognitive and mental flexibility, attention, scanning, and cognitive set shifting can be improved, in particular in a Alzheimer's or dementia patient. WO 2012/125020 discloses a similar product for use in the prevention or treatment of neurotrauma, traumatic brain injury, cerebral palsy and spinal cord injury.

In the art, focus of attention has been on subjects suffering from or at immediate risk of developing dementia and/or Alzheimer's Disease [AD]. As for instance addressed in EP 1.800.675 [N.V. Nutricia], dementia and AD are associated with shrinkage of the brain volume and in particular of the volume of the white matter. Neurodegeneration associated with the above neurodegenerative disorders typically results in death of neurons and a generalized form of cerebral atropy and volume loss, while damaged neurons, including their myelinated axons will be removed from the brain. Such pathology is therefore characterized by a generalized localization and a generalized loss in volume or mass (brain "shrinkage"). The neurodegeneration is commonly associated with the formation of protein agglomerates, which manifest themselves as amyloid plaques or Lewy bodies. When applying brain imaging of such affected brains one typically observes less white matter but also larger ventricles and morphological changes in the grey matter, and optical representations of the protein agglomerates. Volume loss of white matter is recognized to be a pathology that differs from the rather localized hyperintensities around the lateral ventricles in brain, which are frequently observed in elderly, even when they do not experience neurodegeneration.

Multiple sclerosis is also considered to affect white matter, due to a fierce reaction of the immune system on the myelin sheaths of neurons, either present centrally or in peripheral tissues. Such white matter pathology is characterized by a general nature in localization and a consistent decrease in quality of the myelin sheath during the progression of the pathology, caused by a progressing decrease in thickness of the myelin sheaths. The loss of quality can be assessed by measuring for example the speed of transmission of nerve signals. Again, it is pathologically distinct from WMH, Leukoaraiosis or periventricular white matter disease.

There remains a need to target age-associated white matter lesions, white matter hyperintensities (WMH), Leukoaraiosis or periventricular white matter disease in the art.

SUMMARY OF THE INVENTION

The inventors have observed that a product comprising (i) one or more of uridine and cytidine, or salts, phosphates, acyl derivatives or esters thereof, and optionally (ii) a lipid fraction comprising at least one of docosahexaenoic acid (22:6; DHA), eicosapentaenoic acid (20:5; EPA) and docosapentaenoic acid (22:5; DPA), or esters thereof, upon administration can control or reduce Nogo-A protein levels (FIG. 1). Nogo-A is an important protein expressed in hippocampus and oligodendrocytes and held responsible for regulating myelin stabilisation and/or myelin formation. It is a major target for the pharmaceutical industry. It is preferred that the product further comprises at least one of (iii) choline, or salts or esters thereof; or (iv) at least one vitamin B selected from the group of vitamin B6, vitamin B12 and vitamin B9, or equivalents thereof, preferably comprising vitamin B6, B9 and B12. The product preferably comprises both (iii) choline, or salts or esters thereof; and (iv) at least one vitamin B selected from the group of vitamin B6, vitamin B12 and vitamin B9, or equivalents thereof, preferably vitamin B6, B9 and B12.

In the art, Nogo-A protein is known to be one of the three main protein products of reticulon 4, also known as the Neurite outgrowth inhibitor. The membrane protein Nogo-A has been characterized as a central nervous system (CNS)-specific inhibitor of axonal regeneration. It regulates neurite growth and branching in developing nervous system, particularly in the hippocampus, and has a growth-restricting function during CNS maturation. It has a stabilizing function for the neurite network by acting as a growth suppressor. Research has suggested that blocking Nogo-A protein during neuronal damage will help to protect or restore the damaged neurons. It has also been identified as a key component in the process wherein physical exercise enhanced learning and memory processes in the brain. The hippocampus function could thus be improved, particularly in subjects suffering from impaired hippocampus function. As the hippocampus plays an important role in spatial orientation and olfaction, blocking of Nogo-A protein will have its effect there.

Suppression of Nogo or Nogo receptor function has been shown to enhance regenerative sprouting and growth of lesioned fibres after spinal cord or brain injury. Reference is made to Karnezis et al. "*The neurite outgrowth inhibitor Nogo A is involved in autoimmune-mediated demyelination*" Nature Neuroscience 7, 736-744 (2004) and Schwab "*Functions of Nogo proteins and their receptors in the nervous system*" Neuroscience 11, 799-811 (2010). Their contents are herewith incorporated by reference.

Consequently, the inventors found that the effects on Nogo-A are useful in treating, preventing and/or reducing the risk of white matter lesions, white matter hyperintensities (WMH), Leukoaraiosis or periventricular white matter disease. These WMH and lesions represent morphological changes to brain which are considered to be signals of impaired brain function and, dependent on size and localization, can create specific symptoms, which are mediated by the affected brain region. White matter lesions, white matter hyperintensities (WMH), Leukoaraiosis or periventricular white matter disease are particular 'ageing' problems to elderly, different from neurodegeneration-related white matter loss.

As addressed in the background to the invention, volume loss of white matter associated with neurodegenerative disorders such as AD or dementia is recognized to be a pathology that differs from the rather localized hyperintensities around the lateral ventricles in brain which are frequently observed in elderly due to ageing, even occurring when the elderly are not suffering from any neurodegenerative disorders. The skilled person is well capable of distinguishing these age-associated hyperintensities from neurodegenerative disorders and find guidance in the field, such as in the DSM-V list discussed below.

Leukoaraiosis is associated with the micro-vascular problems in regions in the brain around the ventricles. Typically locally a particular region in the brain is affected; the region that was provided with blood by the affected microvessel. The affected region will include local glial- and neural cells and the immune system will locally repair function and remove dead tissue, as far as possible and a lesion in the white matter can develop. When applying brain imaging techniques in such affected brain, this lesion can be observed. When several of these microvascular problems have occurred in time in the brain, several lesions can be observed in the white matter.

In another aspect, the insights provided by the inventors aid in improving hippocampus function and preventing/treating/reducing the risk of occurrence of olfaction malfunction in elderly not suffering from a neurodegenerative disorder such as defined here below, preferably non-AD and non-dementia patients.

LIST OF PREFERRED EMBODIMENTS

In a first aspect, the invention pertains to the use of one or more of uridine and cytidine, or salts, phosphates, acyl derivatives or esters thereof, in the manufacture of a composition for treating, preventing or reducing the risk of occurrence of white matter lesions, white matter hyperintensities (WMH), Leukoaraiosis or periventricular white matter disease in elderly not suffering from a neurodegenerative disorder, preferably non-demented elderly. Alternatively, the invention pertains to a method for treating, preventing or reducing the risk of occurrence of white matter lesions, white matter hyperintensities (WMH), Leukoaraiosis or periventricular white matter disease in elderly not suffering from a neurodegenerative disorder, preferably non-demented elderly, said method comprising administering to said elderly a composition comprising one or more of uridine and cytidine, or salts, phosphates, acyl derivatives or esters thereof. Alternatively, the invention pertains to a composition for use in treating, preventing or reducing the risk of occurrence of white matter lesions, white matter hyperintensities (WMH), Leukoaraiosis or periventricular white matter disease in elderly not suffering from a neurodegenerative disorder, preferably non-demented elderly, said composition comprising one or more of uridine and cytidine, or salts, phosphates, acyl derivatives or esters thereof. The use/method preferably involves controlling, reducing or suppressing Nogo-A protein levels.

In a second aspect, the invention pertains to the use of one or more of uridine and cytidine, or salts, phosphates, acyl derivatives or esters thereof, in the manufacture of a composition for improving hippocampus function and/or preventing/reducing the risk of hippocampus dysfunction in elderly not suffering from a neurodegenerative disorder, preferably non-demented elderly. Alternatively, the invention pertains to a method for improving hippocampus function and/or preventing/reducing the risk of hippocampus dysfunction in elderly not suffering from a neurodegenerative disorder, preferably non-demented elderly, said method comprising administering to said elderly a composition comprising one or more of uridine and cytidine, or salts, phosphates, acyl derivatives or esters thereof. Alternatively, the invention pertains to a composition for use in improving hippocampus function and/or preventing/reducing the risk of hippocampus dysfunction in elderly not suffering from a neurodegenerative disorder, preferably non-demented elderly, said composition comprising one or more of uridine and cytidine, or salts, phosphates, acyl derivatives or esters thereof. The improvements in hippocampus function are associated with Nogo-A protein suppression.

In a third aspect, the invention pertains to the use of one or more of uridine and cytidine, or salts, phosphates, acyl derivatives or esters thereof, in the manufacture of a composition for controlling, reducing or suppressing Nogo-A protein levels in elderly, preferably elderly which are at increased risk of or suffering from amyotrophic lateral sclerosis (ALS) or multiple sclerosis (MS). Alternatively, the invention pertains to a method for controlling, reducing or suppressing Nogo-A protein levels in elderly, preferably elderly which are at increased risk of or suffering from ALS or MS, said method comprising administering to said elderly a composition comprising one or more of uridine and cytidine, or salts, phosphates, acyl derivatives or esters thereof. Alternatively, the invention pertains to a composition for use in controlling, reducing or suppressing Nogo-A protein levels in elderly, preferably elderly which are at increased risk of or suffering from ALS or MS, said composition comprising one or more of uridine and cytidine, or salts, phosphates, acyl derivatives or esters thereof. It is preferred that the Nogo-A protein levels are downregulated or reduced to less than 60%, more preferably less than 50% of control levels, i.e. prior to intervention. The composition used in these aspects is further detailed here below.

In the above embodiments, the composition preferably further comprises a lipid fraction comprising at least one of docosahexaenoic acid (22:6; DHA), eicosapentaenoic acid (20:5; EPA) and docosapentaenoic acid (22:5; DPA), or esters thereof, and optionally (a) choline, or salts or esters thereof; and/or (b) at least one vitamin B selected from the group of vitamin B6, vitamin B12 and vitamin B9, or equivalents thereof. The composition preferably comprises vitamin B6, B9 and B12. Most preferably, the composition comprises at least uridine or UMP, and further DHA, choline, B6, B9 and B12.

In the above embodiments, the method may involve identifying an elderly subject not suffering from a neurodegenerative disorder. The method may also involve assessment of the occurence of and/or quantify the amount of white matter lesions and/or WMH using imaging techniques such as MRI and/or diffusion tensor imaging (DRI).

DETAILED DESCRIPTION OF THE INVENTION

Figure 1A:
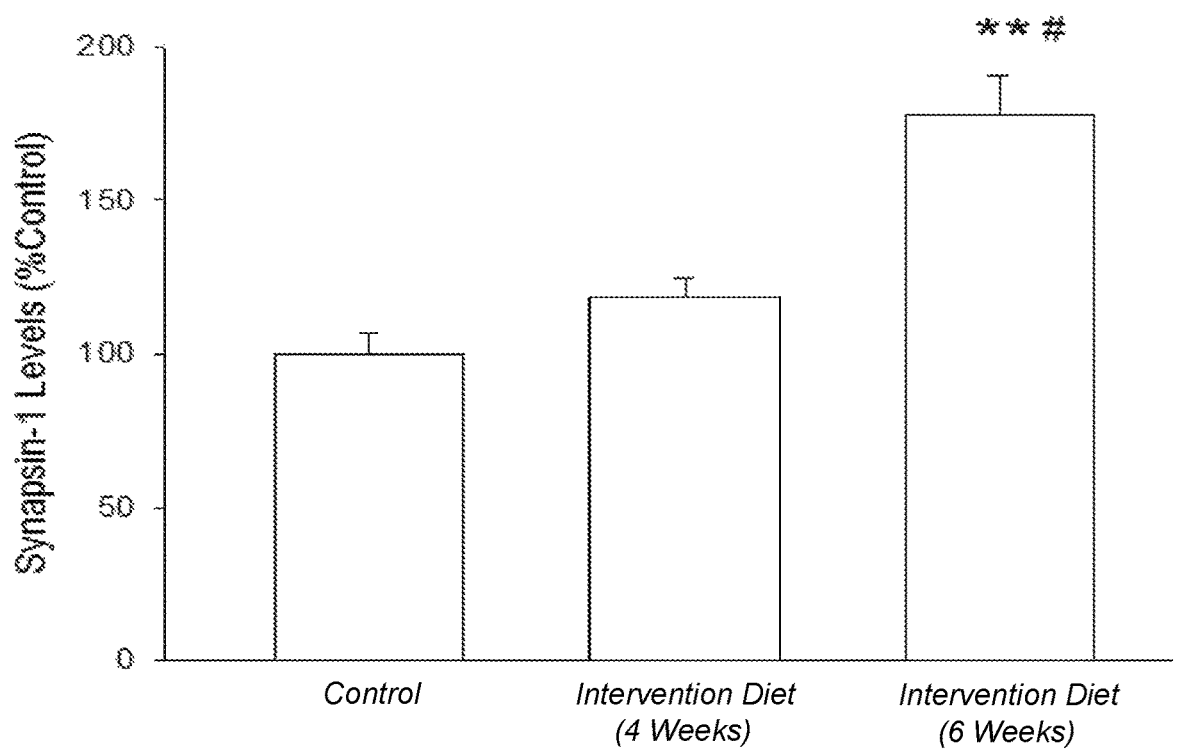
FIGS. 1a, 1b, and 1c show levels of synaptic proteins in the hippocampus were studied over intervention time span of 6 weeks. Synapsin-1 (A), PSD-95 (B) and Nogo-A (C) were assayed by Western blot using homogenues of left hippocampus. *p<0.05 and **p<0.001 compared with Control group, and #p<0.05 compared with 4 weeks intervention diet group.

With the terminology "white matter lesions", "white matter hyperintensities (WMH)", "Leukoaraiosis" and "periventricular white matter disease" the invention distinguishes from those brain and particularly white matter issues (such as white matter brain shrinkage) associated with neurodegenerative disorders, but identify that the invention rather relates to the pathological issues associated with ageing. In the context of the invention, the above terms are regarded interchangeable as it is commonly appreciated in the art. White matter lesions, WMH, Leukoaraiosis and periventricular white matter disease are regarded age-associated periventricular issues, and it is particularly the elderly which are at increased risk thereof. It is reiterated that leukoaraiosis is associated with the micro-vascular problems in regions in the brain around the ventricles. Typically locally a particular region in the brain is affected; the region that was provided with blood by the affected microvessel. The affected region will include local glial- and neural cells and the immune system will locally repair function and remove dead tissue, as far as possible and a lesion in the white matter can develop. When applying brain imaging techniques such as MM or DTI these losses of white matter (lesions, WMH) can be assessed.

Leukoaraiosis, periventricular white matter disease, WMH and white matter lesions according to the invention are distinct from neurodegeneration associated with neurodegenerative disorders which typically results in death of neurons and a generalized form of cerebral atropy and volume loss, while damaged neurons, including their myelinated axons will be removed from the brain. These neurodegenerative disorders are characterized by a generalized localization and a generalized loss in volume or mass (brain "shrinkage"), and the neurodegeneration is commonly associated with the formation of protein agglomerates, which manifest themselves as amyloid plaques or Lewy bodies. Consequently, the subjects are preferably not suffering from a neurodegenerative disorder. In one embodiment, the subject according to the invention is not suffering from a degenerative neurocognitive disorder such as disorders comprising or consisting of AD, Mild Cognitive Impairment (MCI), Parkinson's Disease, Huntington's disease, not suffering from a neurocognitive disorder such as Age Associated Memory Impairment (AAMI), Semantic Dementia or Vascular dementia, not suffering from neurodevelopmental disorders such as Attention Deficit/Hyperactivity Disorder or Autism Spectrum Disorder, and not suffering from Depressive disorders such as Depression or Chronic Depressive Disorder. In one embodiment, the subjects are preferably not suffering from a neurodegenerative disorder selected from AD, dementias, MCI, memory disorders, Parkinson, obsessive compulsive disorder, Tourette's syndrome, depression, schizophrenia, Autism Spectrum Disorders (ASD), post traumatic stress syndrome (PTSD), traumatic brain injury, PKU, alcoholism, Down syndrome, epilepsy, HIV, bipolar disorder, Huntington, attention-deficit/hyperactivity disorder, and autism (asperger). In one embodiment, the subject does not suffer from any of the disorders in this paragraph. In the context of the present invention, a subject not suffering from a certain neurodegenerative disorder may be interpreted as a subject not being diagnosed with said neurodegenerative disorder, such as not diagnosed with any of the disorders in this paragraph.

The 'elderly' are preferably human subjects of at least 50 years of age, more preferably at least 55 years of age, thus reflecting the age-associated character of the WMH.

The elderly are preferably non-demented elderly, wherein the term 'non-demented elderly' in the context of the invention is understood to mean that the elderly are not suffering from dementia or AD, which means that AD or dementia has not been diagnozed. Those human subjects diagnozed/suffering from neurodegenerative disorders such as the above, particularly AD or dementia, are preferably excluded. Elderly can include individuals which are apparently healthy and not demonstrating symptoms of disease. In a different embodiment they can be individuals without abnormal biomarkers like high blood pressure or hyperhomocysteinemia. In a third embodiment these elderly can be persons suffering from diabetes or obesity. Preferably, the subject is drug-naïve, i.e. not on medication dedicated to the treatment of cognitive dysfunction or symptoms thereof.

In one aspect of the present invention, the composition according to the invention may be used as a pharmaceutical product comprising one or more pharmaceutically acceptable carrier materials. Such product may contain the daily dosage in one or more dosage units. The dosage unit may be in a liquid form or in a solid form, wherein in the latter case the daily dosage may be provided by one or more solid dosage units, e.g. in one or more capsules or tablets. The pharmaceutical product, preferably for enteral application, may be a solid or liquid galenical formulation. Examples of solid galenical formulations are tablets, capsules (e.g. hard or soft shell gelatine capsules), pills, sachets, powders, granules and the like which contain the active ingredient together with conventional galenical carriers. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavouring agents, preservatives, stabilizers, emulsifying agents, buffers and the like may be added in accordance with accepted practices of pharmaceutical compounding. While the individual active ingredients are suitably administered in a single composition, they may also be administered in individual dosage units.

In a preferred aspect of the present invention, the composition according to the invention may be used as a nutritional product, for example as a nutritional supplement, e.g., as an additive to a normal diet, as a fortifier, to add to a normal diet, or as a complete nutrition. The nutritional product preferably comprises at least one component selected from the group of fats, proteins, and carbohydrates. It is understood that a nutritional product differs from a pharmaceutical product by the presence of nutrients which provide nutrition to the subject to which the composition is administered, in particular the presence of protein, fat, digestible carbohydrates and dietary fibres. It may further contain ingredients such as minerals, vitamins, organic acids, and flavouring agents. Although the term "nutraceutical product" is often used in literature, it denotes a nutritional product with a pharmaceutical component or pharmaceutical purpose. Hence, the nutritional composition according to the invention may also be used in a nutraceutical product.

The product of the invention is an enteral composition, intended for oral administration. It is preferably administered in liquid form. In one embodiment, the product comprises a lipid fraction and at least one of carbohydrates and proteins, wherein the lipid composition provides between 20 and 50 energy % of the food product. In one embodiment, the food product is a liquid composition containing between 0.8 and 1.4 kcal per ml.

In one embodiment, the composition further increases levels of pre- and post-synaptic proteins Synapsin-1 and PSD-95, respectively. In one embodiment, these membrane phospholipids and pre- and post-synaptic proteins are not targeted.

UMP

The present composition comprises uridine, cytidine and/or an equivalent thereof, including salts, phosphates, acyl derivatives (e.g. $C_{1-6}$ acylated uridine) and/or esters (e.g. $C_{1-6}$ alkanoate ester). In terms of uridine, the composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied. Preferably, the present composition comprises an uridine phosphate selected from the group consisting of uridine monophosphate (UMP), uridine diphosphate (UDP) and uridine triphosphate (UTP); and/or a cytidine phosphate (CMP, CDP, CTP, preferably CMP). Most preferably the present composition comprises UMP, as UMP is most efficiently being taken up by the body. Preferably at least 50 weight % of the uridine in the present composition is provided by UMP, more preferably at least 75 weight %, most preferably at least 95 weight %. Doses that must be administered are given as UMP. The amount of uracil sources can be calculated taking the molar equivalent to the UMP amount.

The present method preferably comprises the administration of uridine (the cumulative amount of uridine, deoxyuridine, uridine phosphates, nucleobase uracil and acylated uridine derivatives) in an amount of (i) 0.1 to 6 g per day, preferably 0.2 to 3 g per day, more preferably 0.4 to 2 g per day, and/or (ii) 0.1 to 6 g per 100 ml (liquid) composition, preferably 0.2 to 3 g per 100 ml (liquid) composition, more preferably 0.4 to 2 g per 100 ml (liquid) composition. In one embodiment, the above amounts also account for any amounts of cytidine, cytidine phosphates and citicoline incorporated in the composition or method. Uridine and its equivalents are however preferred.

Preferably, the present composition comprises uridine phosphate, preferably uridine monophosphate (UMP). The UMP is very efficiently taken up by the body. Hence, inclusion of UMP in the present composition enables a high effectivity at the lowest dosage and/or the administration of a low volume to the subject.

DHA/EPA

The composition preferably comprises at least one ω-3 polyunsaturated fatty acid (LC PUFA; having a chain length of 18 and more carbon atoms) selected from the group consisting of docosahexaenoic acid (22:6; DHA), eicosapentaenoic acid (20:5; EPA) and docosapentaenoic acid (22:5 ω-3; DPA), preferably at least one of DHA and EPA. Preferably the present composition contains at least DHA, more preferably DHA and EPA. EPA is converted to DPA (ω-3), increasing subsequent conversion of DPA to DHA in the brain. Hence, the present composition preferably contains a significant amount of EPA, so to further stimulate in vivo DHA formation.

The DHA, EPA and/or DPA are preferably provided as triglycerides, diglycerides, monoglycerides, free fatty acids or their salts or esters (e.g. $C_{1-6}$ alkyl ester), phospholipids, lysophospholipids, glycerol ethers, lipoproteins, ceramides, glycolipids or combinations thereof. Preferably, the present composition comprises at least DHA in triglyceride form.

In terms of daily dosage, the present method preferably comprises the administration of 500 to 5000 mg DHA+EPA+DPA (preferably DHA+EPA) per day, more preferably 750 to 4000 mg per day, most preferably 1000 to 3000 mg per day. DHA is preferably administered in an amount of 500 to 5000 mg per day, more preferably 750 to 4000 mg per day, most preferably 1000 to 3000 mg per day. If at all, EPA is preferably administered in an amount of 500 to 5000 mg per day, more preferably 750 to 4000 mg per day, most preferably 1000 to 3000 mg per day. These amounts of EPA apply if it is used alone or in combination with DHA.

In terms of unit dosage, the proportion of DHA+EPA+DPA (preferably DHA+EPA) of the total fatty acids is preferably 5 to 95 weight %, more preferably 10 to 80 weight %, most preferably 15 to 70 weight %. The present composition preferably comprises 5 to 95 weight % DHA based on total fatty acids, preferably 10 to 75 weight % DHA based on total fatty acids, more preferably 10 to 60 weight % DHA based on total fatty acids. The present composition preferably comprises 5 to 95 weight % EPA based on total fatty acids, preferably 10 to 75 weight % EPA, most preferably 15 to 60 weight %, based on total fatty acids.

The ratio of the weights of DHA to EPA is preferably larger than 1, more preferably 2:1 to 10:1, more preferably 3:1 to 8:1. The above-mentioned ratios and amounts take into account and optimise several aspects, including taste (too high LCP levels reduce taste, resulting in a reduced compliance), balance between DHA and precursors thereof to ensure optimal effectiveness while maintaining low-volume formulations. Sources of DHA possible sources of DHA: tuna oil, (other) fish oils, DHA rich alkyl esters, algae oil, egg yolk, or phospholipids enriched with n-3 LCPUFA e.g. phosphatidylserine-DHA.

ALA/LA

It is preferred that the alpha-linolenic acid [ALA] content of the composition is maintained at low levels. The inventors believe that due to the inflammatory nature of neurotrauma, excess supply of highly unsaturated fatty acids increases the risk of further damage to injury tissue due to the effect of peroxidized PUFAs, even though it has been observed that in vivo supply of α-linolenic acid is neuroprotective in neurotrauma (King et al. *J. Neurosci.* (26) 17:4672-4680). The ALA concentration is preferably maintained at levels less than 2.0 weight %, more preferably below 1.5 weight %, particularly below 1.0 weight %, calculated on the weight of all fatty acids.

Linoleic acid [LA] concentrations can be maintained at normal levels, i.e. between 20 to 30 weight %, although in one embodiment the LA concentration is also significantly reduced to an amount of <15 g/100 g fatty acids and even less than 10 weight %. The LA concentrations are preferably at least 1 weight % of the fatty acids.

In one embodiment, the weight ratio ω-3/ω-6 in the composition of the invention is preferably in the range 0.3 to 7, preferably in the range 1.4:1 to 5.9:1, more preferably in the range 3:1 to 5.5:1, most preferably 3:1 to 5:1, in particular less than 5:1. The amount of ω-6 LCPUFAs is preferably less than 50, preferably 5 to 40, more preferably 8 to 30 weight % of the fatty acids in the formula.

MCT

In one embodiment, the composition contains less than 5 weight %, preferably less than 2 weight % of fatty acids of less than 14 carbon atoms. Medium chain fatty acids [MCT] are defined to be linear or branched saturated carboxylic acids having six (C6:0), seven (C7:0), eight (C8:0), nine (C9:0) or ten (C10:0) carbon atoms. The amount of MCTs are preferably lower than 2 weight %, more preferably lower than 1.5 weight %, most preferably lower than 1.0 weight % of the total fatty acids. In one embodiment, the sum of the medium chain fatty acids C6:0+C7:0+C8:0 over the sum of C9:0 and C10:0 is less than 2:1, more preferably less than 1.8:1, most preferably less than 1.6:1.

Choline

The present composition preferably contains choline, a choline salt and/or choline ester (e.g. $C_{1-6}$ alkanoate ester). The choline salt is preferably selected from choline chloride, choline bitartrate, or choline stearate. The choline ester is preferably selected from a phosphatidylcholine and lyso-phosphatidyl choline. The present method preferably comprises the administration of more than 50 mg choline per day, preferably 80 to 3000 mg choline per day, more preferably 100 to 2000 mg choline per day, most preferably 150 to 1000 mg choline per day. The present composition preferably comprises 80 mg to 3000 gram choline per 100 ml of the liquid composition, preferably 100 mg to 2000 mg choline per 100 ml, preferably 200 to 1000 mg choline per 100 ml composition, most preferably 200 mg to 600 mg choline per 100 ml. The above numbers are based on choline, the amounts of choline equivalents or sources can be calculated taking the molar equivalent to choline into account.

B vitamins

The present combination preferably comprises at least one B complex vitamin. The vitamin B is selected from the group of vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid or folate), and vitamin B12 (various cobalamins). Functional equivalents are encompassed within these terms.

Preferably, at least one vitamin B is selected from the group of vitamin B6, vitamin B12 and vitamin B9. Preferably the present composition comprises at least two selected from the group consisting of vitamin B6, vitamin B12 and vitamin B9. In particular, good results have been achieved with a combination comprising vitamin B6, vitamin B12 and vitamin B9.

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (IOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose usually does not exceed the tolerable upper intake levels (UL), as recommended by IOM.

If present in the nutritional composition or medicament, the vitamin B6 is usually present in an amount to provide a daily dosage in the range of 0.1 to 100 mg, in particular in the range of 0.5 to 25 mg, more in particular in the range of 0.5 to 5 mg. The present composition preferably comprises 0.1 to 100 mg vitamin B6 per 100 g (liquid) product, more preferably 0.5 to 5 mg vitamin B6 per 100 g (liquid) product, more preferably 0.5 to 5 mg vitamin B6 per 100 g (liquid) product.

If present in the nutritional composition or medicament, the vitamin B12 is usually present in an amount to provide a daily dosage in the range of 0.5 to 100 μg, in particular in the range of 1 to 10 μg, more in particular in the range of 1.5 to 5 μg. The present composition preferably comprises 0.5-100 μg vitamin B12 per 100 g (liquid) product, more preferably 1 to 10 μg vitamin B12 per 100 g (liquid) product, more preferably 1.5 to 5 μg vitamin B12 per 100 g (liquid) product. The term "vitamin B12" incorporates all cobalamin equivalents known in the art.

If present in the nutritional composition or medicament, the vitamin B9 is usually present in an amount to provide a daily dosage in the range of 50 to 5000 μg, in particular in the range of 100 to 1000 μg, more in particular in the range of 200 to 800 μg. The present composition preferably comprises 50 to 5000 μg folic acid per 100 g (liquid) product, more preferably 100 to 1000 μg folic acid per 100 g (liquid) product, more preferably 200 to 800 μg folic acid per 100 g (liquid) product. Folates include folic acid, folinic acid, methylated, methenylated and formylated forms of folates, their salts or esters (e.g. $C_{1-6}$ alkyl ester), as well as their derivatives with one or more glutamic acid, and all in either reduced or oxidized form.

Phospholipids

It is preferred to incorporate at least one phospholipid in the composition. The term "phospholipid" excludes PC that is already accounted for in the choline fraction. The present composition preferably comprises at least one phospholipid in an amount of 0.01 to 1 gram per 100 ml, more preferably between 0.05 and 0.5 gram per 100 ml, most preferably 80 to 600 mg per 100 ml. The at least one phospholipid is preferably provided for using lecithin.

Vitamins C, E

Vitamin C, or a functional equivalent thereof, may be present in an amount to provide a daily dosage in the range of 20 to 2000 mg, in particular in the range of 30 to 500 mg, more in particular in the range of 75 to 150 mg. In one embodiment, vitamin C, or a functional equivalent thereof, is present in an amount in the range of 20 to 2000 mg, in particular in the range of 30 to 500 mg, more in particular in the range of 75 to 150 mg per 100 ml of the composition.

Tocopherol and/or an equivalent thereof (i.e. a compound having vitamin E activity) may be present in an amount to provide a daily dosage in the range of 10 to 300 mg, in particular in the range of 30 to 200 mg, more in particular in the range of 35 to 100 mg, to prevent oxidative damage to the injury site resulting from dietary PUFA. In one embodiment, tocopherol and/or equivalent is present in an amount in the range of 10 to 300 mg, in particular in the range of 30 to 200 mg, more in particular in the range of 35 to 100 mg per 100 ml of the composition. The term "tocopherol and/or an equivalent thereof", as used in this description, comprises tocopherols, tocotrienols, pharmaceutical and/or nutritional acceptable derivatives thereof and any combination thereof. The above numbers are based on tocopherol equivalents, recognized in the art.

Selenium

The present composition preferably contains selenium. The antioxidant activity of selenium advantageously prevents and/or inhibits damages to the brain areas. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01 to 0.5 mg.

In view of the above, the composition according to the invention preferably comprises uridine and/or UMP, the omega-3 PUFAs DHA and EPA, choline, phospholipids, folic acid, vitamin B12 and vitamin B6, in any of the aforementioned forms, equivalents or derivatives. The composition preferably comprises uridine and/or UMP, the omega-3 PUFAs DHA and EPA, choline, phospholipids, folic acid, vitamin B12, vitamin B6, vitamin C, vitamin E, and selenium, in any of the aforementioned forms, equivalents or derivatives.

In one embodiment, the composition according to the invention comprises per daily dosage or per 100 ml of liquid (preferably water):

- 100-500 mg, preferably 200-400 mg, more preferably about 300 mg EPA,
- 900-1500 mg, preferably 950-1300 mg, more preferably about 1200 mg DHA,
- 50-600 mg, preferably 60-200 mg, more preferably about 106 mg phospholipids,
- 200-600 mg, preferably 300-500 mg, more preferably about 400 mg choline,
- 400-800 mg, preferably 500-700 mg, more preferably about 625 mg UMP (uridine monophosphate),
- 20-60 mg, preferably 30-50 mg, more preferably about 40 mg vitamin E (alpha-TE),
- 60-100 mg, preferably 60-90 mg, more preferably about 80 mg vitamin C,
- 40-80 μg, preferably 45-65 μg, more preferably about 60 μg selenium,
- 1-5 μg, preferably 2-4 μg, more preferably about 3 μg vitamin B12,
- 0.5-3 mg, preferably 0.5-2 mg, more preferably about 1 mg vitamin B6, and
- 200-600 μg, preferably 300-500 μg, more preferably about 400 μg folic acid.

The compositions as described above can be used as a nutritional therapy, nutritional support, as a medical food, as a food for special medical purposes or as a nutritional supplement. Such product can be consumed at one, two or three servings of 125 mL per day during recovery and/or rehabilitation in the context of the impairments according to the invention.

Preferably, the composition is enterally administered to the elderly at least one time per day for a period of at least 3 weeks, preferably at least 4 weeks, more preferably at least 5 weeks, particularly at least 6 weeks.

EXAMPLES

Example 1. Experimental Evidence. Rat Study

Methods

Animals

Eighteen-month-old male Wistar rats (Experimental Animals Breeding and Research Center, Uludag University Medical School, Bursa, Turkey) were group-housed in a temperature controlled room with free access to standard rat chow and water under a 12 h light/dark cycle. The experimental protocol was approved by the Animal Care and Use Committee of Uludag University, Bursa, Turkey (Approval ID: 2012-03/03), and all experiments conformed to the National Institutes of Health Guide for the Care and Use of Laboratory Animals (NIH Publications No. 80-23) revised 1996. All efforts were made to minimize the number of animals used and the individual level of discomfort.

Dietary Supplementation

Rats were randomized to Control and Invention diet groups; rats in the Control group (n=4) were supplemented with regular rat chow for 4 weeks while rats in the 'invention' group were fed the intervention diet for either 4 (n=5) or 6 (n=5) weeks. Both the Control diet and the intervention diet were AIN-93 M based (Reeves 1993), isoenergetic, and fulfilled all dietary requirements. Both diets contained the standard vitamin mix (AIN-93-VX) and mineral mix (AIN-93M-MX). The diets differed in composition with regard to the fat blends used, as well as a number of supplemented nutrients, including choline, B-vitamins, antioxidants, UMP, and lecithin. A detailed overview of the contents of diets has been presented in Table 1. The diets were formulated by Nutricia Advanced Medical Nutrition, Nutricia Research (Utrecht, the Netherlands) and manufactured by Ssniff Spezialdiaten (Soest, Germany) and were presented to the animals as pellets. All diets were stored at −20° C. until use, in order to prevent oxidation of lipids. Reanalysis of the diets at the end of the study confirmed that all fatty acids were still present in the original amounts.

No significant difference was observed between treatment groups in terms of mean daily amount of food consumed and weight gain during the treatment protocol.

TABLE 1

Detailed compositions of the two experimental diets (in g/100 g diet)

| Ingredients (g/100 g diet) | Diets | |
|---|---|---|
|  | Control | Intervention |
| Cornstarch, pre-gelatinized | 35.6 | 32.5 |
| Caseine | 14.0 | 14.0 |
| Maltodextrin, 10 DE | 15.5 | 15.5 |
| Sucrose | 10.0 | 10.0 |
| Dextrose | 10.0 | 10.0 |
| Soy oil | 1.900 |  |
| Coconut oil | 0.900 | 0.100 |
| Corn oil | 2.200 | 1.700 |
| Fish oil |  | 3.200 |
| Cellulose powder | 5.0 | 5.0 |
| Mineral mix (AIN-93M-MX) | 3.5 | 3.5 |
| Vitamin mix (AIN-93-VX) | 1.0 | 1.0 |
| L-cystine | 0.180 | 0.180 |
| Choline chloride (50%) | 0.230 | 0.922 |
| Tert-butylhydroquinone | 0.0008 | 0.0008 |
| UMP (UMP disodium salt) |  | 1.0 |
| Soy lecithin |  | 0.755 |
| Vitamin B6 (pyridoxin hydrochloride, 100%) |  | 0.00328 |
| Folic acid (100%) |  | 0.00060 |
| Vitamin B12 (cyanocobalamin, 0.1%) |  | 0.00350 |

TABLE 1-continued

Detailed compositions of the two experimental diets (in g/100 g diet)

| Ingredients (g/100 g diet) | Diets | |
| --- | --- | --- |
| | Control | Intervention |
| Ascorbic acid (100%) | | 0.160 |
| Vitamin E (tocopherol acetate, 50%) | | 0.4650 |
| Selenium (sodium selenite pentahydrate, 100%) | | 0.00034 |
| Total | 100.0 | 100.0 |

Surgical Procedures

One day prior to completion of dietary treatment, a probe was inserted in the right hippocampus of rats in each group to perform in vivo microdialysis. Rats were anesthetized with Ketamine and Xylazine (80 mg/kg and 10 mg/kg, respectively) and then placed in a stereotaxic frame. Subsequently, skulls were exposed and a small hole was drilled over the right hippocampus. A hand-made probe (molecular weight cutoff of dialysis membrane was 13,000 Da and length was 1 mm) was implanted in the CA1 region of the hippocampus by using Dura at Bregma as the reference point (coordinates were: AP −4.0 mm; ML −2.2 mm; DV 2.6 mm; Paxinos and Watson, 2004) and then fixed to the skull using acrylic cement. After surgery the rats were placed in individual cages and allowed to recover from anesthesia for 24 h. During this period, they remained calm and showed no signs of overt discomfort or pain.

In Vivo Microdialysis

In vivo microdialysis experiments were carried out 24 h after surgery to avoid effects of anesthesia. The dialysis probe inserted in CA1 region of the right hippocampus of freely-moving rats was perfused at a rate of 2 μL/min with artificial cerebrospinal fluid (CSF; pH=7.4) of the following composition: 148 mM NaCl, 3.0 mM KCl, 1.4 mM $CaCl_2$, 0.8 mM $MgCl_2$, 1.3 mM $NaH_2PO_4$, 0.2 mM $Na_2HPO_4$ and neostigmine (1 μM) to block enzymatic degradation of ACh.

Each microdialysis sample was collected with 30 min intervals. Samples collected during the first hour of microdialysis were discarded. After collection of the first three microdialysates, which were referred to as baseline samples, the perfusion medium was replaced with another which contained atropine sulfate (10 μM). This perfusion was continued for 1 h and then atropine-containing medium was replaced with the initial atropine-lacking medium.

Microdialysis was terminated at the end of 6 h after the start of collecting the first baseline sample and rats were sacrificed under Ketamine and Xylazine (80 mg/kg and 10 mg/kg, respectively) anesthesia. Brains were immediately taken out and left hippocampi were obtained, weighed and homogenized in 50 volumes of ice-cold deionized water with 10 up-and-down strokes, using a teflon-glass homogenizer (Wheaton, Milville, N.J., USA) in order to assay levels of synaptic proteins.

Western Blot Analysis

Synaptic proteins were assayed by Western Blot as described previously (Wurtman et al., 2006; Sakamoto et al., 2007). Briefly, aliquots of hippocampal homogenates were mixed with equal volumes of Laemmi loading buffer and boiled prior to gel electrophoresis. Equal amounts of protein were loaded and separated using SDS-PAGE (4-20%; Bio-Rad, Hercules, Calif., USA). Proteins were then transferred onto polyvinylidene fluoride (PVDF) membranes (Millipore, Billerica, Mass., USA). The remaining binding sites were blocked with 4% non-fat dry milk (Carnation, Glendale, Calif., USA) for 30 min in Tris-Buffered Saline and Tween 20 (TBST). Membranes were then rinsed five times in TBST buffer and incubated overnight in TBST solution containing the primary antibody of interest (goat anti-PSD-95 [Abcam, Cambridge, Mass., USA; ab90426], rabbit anti-synapsin-1 [Abeam; ab18814] and rabbit anti-Nogo-A [Abeam; ab62024]). Next day, blots were incubated for 1 h with the appropriate peroxidase-linked secondary antibody followed by detection and visualization of protein-antibody complexes using the enhanced chemiluminescence system (GE Healthcare Biosciences, Pittsburgh, Pa., USA) and Kodak X-AR films which were digitized using a Supervista S-12 scanner (UMAX Technologies, Freemont, Calif., USA). Immunoreactive bands were compared densitometrically using the Public Domain NIH Image program available at http://rsb.info.nih.gov/ij/ according to the instructions of the software. Membranes were stripped using a stripping buffer (Thermo Fisher Scientific, Rockford, Ill., USA) and then incubated with beta-tubulin antibody (mouse anti-beta-tubulin [Sigma; T5076]) used as the loading control.

Statistics

Statistical analyses were performed using Sigma Plot software version 12.0. Data were expressed as mean±standard error of means (SEM). All data were analyzed using one-way ANOVA followed by post-hoc Tukey test, except for repetitive data which was analyzed by two-way ANOVA with repeated measures followed by Tukey test. P-values less than 0.05 were considered significant.

Results and Discussion

Figure 1B:
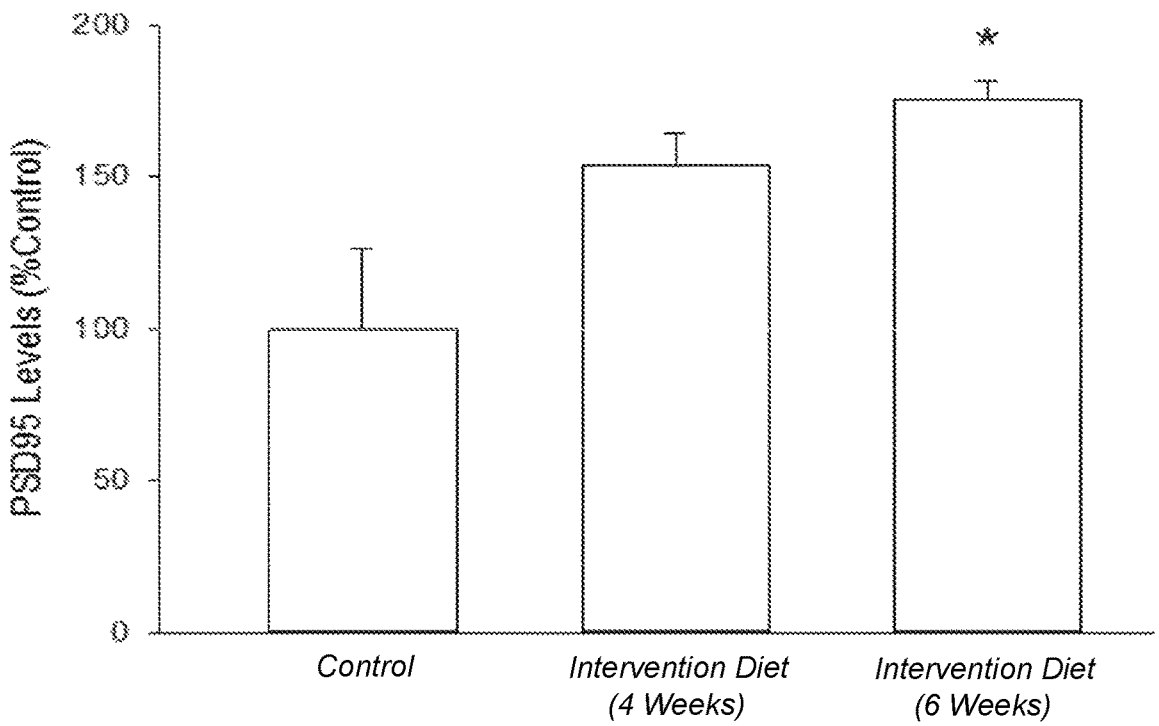
Figure 1C:
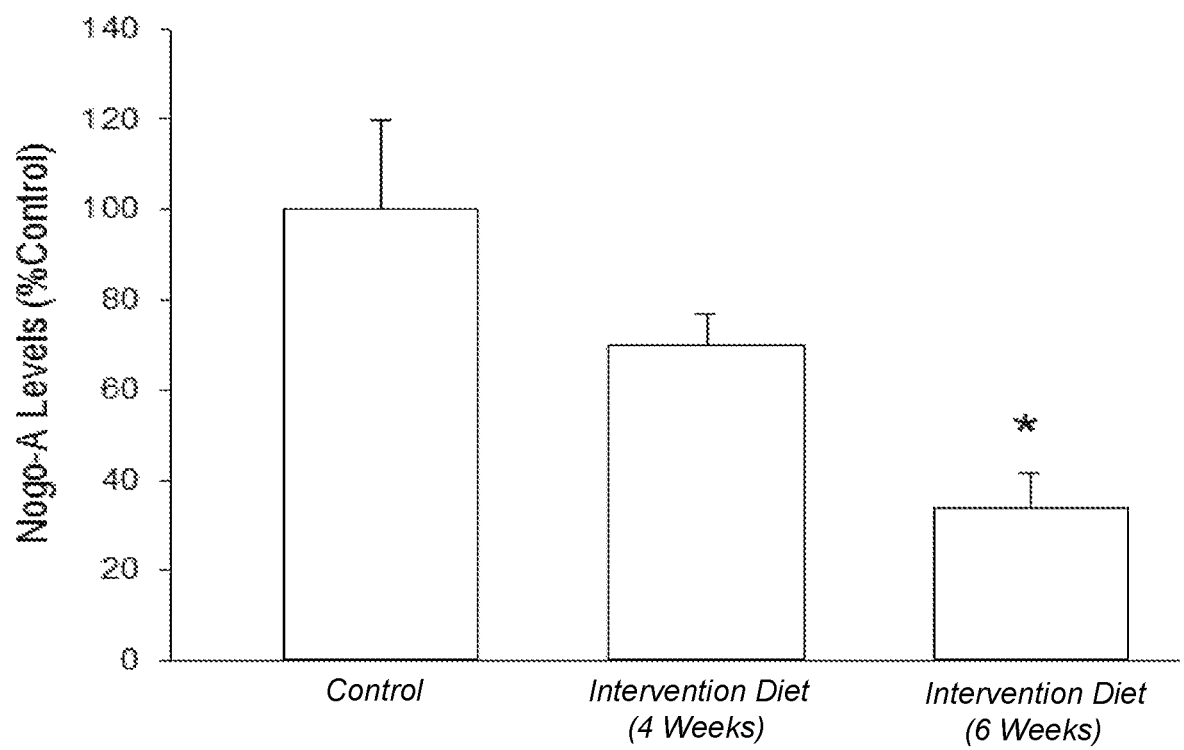

Dietary enrichment with the intervention diet for 6 weeks significantly enhanced levels of pre- and post-synaptic proteins while decreasing those of Nogo-A, a neurite outgrowth inhibitor. Compared with the Control group, levels of Synapsin-1 (FIG. 1A) and PSD-95 (FIG. 1B) were increased by 78% (p<0.001) and 75% (p<0.05) in rats receiving the intervention diet for 6 weeks, respectively. Treatment with intervention diet for 4 weeks already tended to enhance levels of pre- and post-synaptic proteins and decrease those of Nogo-A. The levels of Nogo-A further decreased in 6 weeks intervention group by 66% (p<0.05) (FIG. 1C). The data suggest that the intervention diet not only prevents the blockade by Nogo-A of neurite outgrowth but also help reducing negative effects of Nogo-A on neuronal plasticity and formation of new synaptic contacts, as supported with the evidence on synaptic proteins.

CITED REFERENCES

Reeves, P. G., Nielsen, F. H., Fahey, G. C., Jr., 1993. AIN-93 purified diets for laboratory rodents: final report of the American Institute of Nutrition ad hoc writing committee on the reformulation of the AIN-76A rodent diet. J. Nutr. 123, 1939-1951.

Wurtman, R. J., Ulus, I. H., Cansev, M., Watkins, C. J., Wang, L., Marzloff, G., 2006. *Synaptic proteins and phospholipids are increased in gerbil brain by administering uridine plus docosahexaenoic acid orally*. Brain Res. 1088, 83-92;

Paxinos, G., Watson, C., 2004. *The rat brain in stereotaxic coordinates*, fifth ed. Elsevier, San Diego;

Sakamoto, T., Cansev, M., Wurtman, R. J., 2007. *Oral supplementation with docosahexaenoic acid and uridine-5'-monophosphate increases dendritic spine density in adult gerbil hippocampus*. Brain Res. 1182, 50-59.

Example 2: Preferred Ranges of the Products

TABLE 1

|  | Ranges for claimed products (mg/100 kJ) | Fortifier (mg/100 kJ) | Complete Adult (mg/100 kJ) |
| --- | --- | --- | --- |
| DHA | 7-240 | 50-120 | 120-240 |
| DHA + EPA | 9-300 | 70-150 | 150-300 |
| UMP, CMP | 1.5-130 | 3-130 | 35-130 |
| UMP + CMP | 3-130 | 6-130 | 50-130 |
| Choline | 1-300 | 1-60 | 60-300 |

Example 3a: Liquid Product Containing Per 125 ml Serving

| | |
| --- | --- |
| Fat, g 4.9 | Vitamin E (alpha-TE), mg 40 |
| EPA, mg 300 | Vitamin C, mg 80 |
| DHA, mg 1200 | Selenium, μg 60 |
| Phospholipids, mg 106 | Vitamin B12, μg 3 |
| Choline, mg 400 | Vitamin B6, mg 1 |
| UMP (uridine monophosphate), mg 625 | Folic acid, μg 400 |

Abbreviations:
EPA, eicosapentaenoic acid; DHA, docosahexaenoic acid; TE, tocopherol equivalents.

Example 3b: Liquid Product Containing Per 125 ml Serving

| | |
| --- | --- |
| Energy, kcal 125 | Calcium, mg 100 |
| Protein, g 3.8 | Phosphorus, mg 87.5 |
| Carbohydrate, g 16.5 | Magnesium, mg 25.0 |
| Fat, g 4.9 | Iron, mg 2 |
| EPA, mg 300 | Zinc, mg 1.5 |
| DHA, mg 1200 | Iodine, μg 16.3 |
| Phospholipids, mg 106 | Manganese, mg 0.41 |
| Choline, mg 400 | Copper, μg 225 |
| UMP (uridine monophosphate), mg 625 | Molybdenum, μg 12.5 |
| Vitamin E (alpha-TE), mg 40 | Chromium, μg 8.4 |
| Vitamin C, mg 80 | Vitamin A, μg 200 |
| Selenium, μg 60 | Thiamin (B1), mg 0.19 |
| Vitamin B12, μg 3 | Riboflavin (B2), mg 0.20 |
| Vitamin B6, mg 1 | Niacin (B3), mg NE 2.25 |
| Folic acid, μg 400 | Pantothenic acid (B5), mg 0.66 |
| Sodium, mg 125 | Vitamin D, μg 0.88 |
| Potassium, mg 187.5 | Biotin, μg 5.0 |
| Cloride, mg 156.3 | Vitamin K, μg 6.6 |

Abbreviations:
NE, niacin equivalents.

The invention claimed is:

1. A method for treating a non-demented, elderly subject suffering from white matter hyperintensities (WMH), Leukoaraiosis or periventricular white matter disease, the method comprising administering to the subject a composition comprising, per 100 ml of liquid:
   (a) 600-5000 mg docosahexaenoic acid (DHA),
   (b) 200-600 mg choline,
   (c) 400-800 mg uridine monophosphate (UMP), and
   (d) 200-600 μg folic acid.

2. The method according to claim 1, wherein the composition comprises, per 100 ml of liquid:
   (a) 900-1500 mg DHA,
   (b) 200-600 mg choline,
   (c) 400-800 mg uridine monophosphate (UMP), and
   (d) 200-600 μg folic acid.

3. The method according to claim 1, wherein the administration controls, reduces or suppresses Nogo-A protein levels in the subject.

4. The method according to claim 1, wherein the composition comprises vitamin B6, B9 and B12.

5. The method according to claim 1, wherein the composition further comprises one or more selected from the group consisting of vitamin C or its equivalents, vitamin E or its equivalents, and selenium.

6. The method according to claim 1, wherein the composition further comprises at least one phospholipid.

7. The method according to claim 1, wherein the composition is an aqueous composition comprising, per daily dosage or per 100 ml of liquid:
   100-500 mg EPA,
   900-1500 mg DHA,
   50-600 mg phospholipids,
   200-600 mg choline,
   400-800 mg UMP (uridine monophosphate),
   20-60 mg vitamin E (alpha-TE),
   60-100 mg vitamin C,
   40-80 μg selenium,
   1-5 μg vitamin B12,
   0.5-3 mg vitamin B6, and
   200-600 μg folic acid.

8. The method according to claim 1, wherein the composition is enterally administered to the elderly subject at least one time per day for a period of at least 3 weeks.

9. A method for treating an elderly subject suffering from white matter hyperintensities (WMH), Leukoaraiosis or periventricular white matter disease, the method comprising administering to the subject a composition comprising, per 100 ml of liquid:
   (a) 600-5000 mg docosahexaenoic acid (DHA),
   (b) 200-600 mg choline,
   (c) 400-800 mg uridine monophosphate (UMP), and
   (d) 200-600 μg folic acid,
wherein the subject does not suffer from Alzheimer's Disease.

10. The method according to claim 9, wherein the composition comprises, per 100 ml of liquid:
   (a) 900-1500 mg DHA,
   (b) 200-600 mg choline,
   (c) 400-800 mg uridine monophosphate (UMP), and
   (d) 200-600 μg folic acid.

11. The method according to claim 9, wherein the administration controls, reduces or suppresses Nogo-A protein levels in the subject.

12. The method according to claim 9, wherein the composition comprises vitamin B6, B9 and B12.

13. The method according to claim 9, wherein the composition further comprises one or more selected from the group consisting of vitamin C or its equivalents, vitamin E or its equivalents, and selenium.

14. The method according to claim 9, wherein the composition is an aqueous composition comprising, per daily dosage or per 100 ml of liquid:
   100-500 mg EPA,
   900-1500 mg DHA,
   50-600 mg phospholipids,
   200-600 mg choline, 400-800 mg UMP (uridine monophosphate),
20-60 mg vitamin E (alpha-TE),
60-100 mg vitamin C,
40-80 µg selenium,
1-5 µg vitamin B12,
0.5-3 mg vitamin B6, and
200-600 µg folic acid.

* * * * *